(12) United States Patent
Pahnke et al.

(10) Patent No.: US 9,695,117 B2
(45) Date of Patent: Jul. 4, 2017

(54) FLUOROSURFACTANTS IN PESTICIDES

(71) Applicant: MERCK PATENT GMBH, Darmstadt (DE)

(72) Inventors: Joerg Pahnke, Darmstadt (DE); Gerhard Jonschker, Heppenheim (DE); Steffen Schellenberger, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/895,800

(22) PCT Filed: May 20, 2014

(86) PCT No.: PCT/EP2014/001354
§ 371 (c)(1),
(2) Date: Dec. 3, 2015

(87) PCT Pub. No.: WO2014/194984
PCT Pub. Date: Dec. 11, 2014

(65) Prior Publication Data
US 2016/0122297 A1 May 5, 2016

(30) Foreign Application Priority Data
Jun. 4, 2013 (EP) ..................... 13002875

(51) Int. Cl.
*C07C 317/44* (2006.01)
*A01N 25/30* (2006.01)
*A01N 41/10* (2006.01)

(52) U.S. Cl.
CPC ............ *C07C 317/44* (2013.01); *A01N 25/30* (2013.01); *A01N 41/10* (2013.01)

(58) Field of Classification Search
None
See application file for complete search history.

(56) References Cited

U.S. PATENT DOCUMENTS

| 4,968,599 A | 11/1990 | Pitt et al. |
| 4,988,610 A | 1/1991 | Pitt et al. |
| 5,198,467 A | 3/1993 | Milks |
| 6,221,811 B1 | 4/2001 | Policello et al. |
| 6,890,608 B2 | 5/2005 | Morishima et al. |
| 8,120,833 B2 | 2/2012 | Chan et al. |
| 8,673,819 B2 | 3/2014 | Sun |
| 9,115,062 B2 | 8/2015 | Hierse et al. |
| 2011/0088594 A1 | 4/2011 | Claus et al. |
| 2011/0111961 A1 | 5/2011 | Sun |
| 2012/0008186 A1 | 1/2012 | Chan et al. |
| 2012/0111233 A1 | 5/2012 | Hierse et al. |
| 2013/0269568 A1 | 10/2013 | Claus et al. |

FOREIGN PATENT DOCUMENTS

| CA | 2230769 A1 | 9/1998 |
| DE | 102009030846 A1 | 12/2010 |
| WO | 2009149807 A1 | 12/2009 |
| WO | 2010003889 A1 | 1/2010 |
| WO | 2012003567 A2 | 1/2010 |
| WO | 2010149262 A1 | 12/2010 |
| WO | 2011082770 A2 | 7/2011 |
| WO | 2012084118 A1 | 6/2012 |

OTHER PUBLICATIONS

International Search Report dated Jul. 29, 2014 issued in corresponding PCT/EP2014/001354 application (pp. 1-6).
N. Takafumi, et al., "Perfluoropolyether-containing amphiphilic compounds and their uses", Database Caplus [Online] XP002714401 Database accession No. 2004-52783, (2004) pp. 1.
J. Alexander, et al., Perfluorooctane sulfonate (PFOS), perfluorooctanoic acid (PFOA) and their salts Scientific Opinion of the Panel on Contaminants in the Food chain 1 (Question N o EFSA-Q-2004-163), The EFSA Journal, (2008) pp. 1-131.
F. Stagnari, et al., "Influence of fluorinated surfactants on the efficacy of some post-emergence sulfonylurea herbicides", J. Pestic. Sci. , vol. 32, No. 1 (2007) pp. 16-23.
A.R. Pitt, et al., "The relationship between surfactant structure and limiting values of surface tension, in aqueous gelatin solution, with particular regard to multilayer coating", Colloids and Surfaces A: Physicochemical and Engineering Aspects, vol. 114 (1996) pp. 321-335.
A.R. Pitt, "The efficiency of dynamic surface tension reductions within homologous series of surfactants in aqueous gelatin solution", Progr Colloid Polym Sci, vol. 103 (1997) pp. 307-317.
Z. Liu, et al., "Phase Behaviors of Aerosol-OT Analogue Fluorinated Surfactants in 1, 1, 1, 2-Tetrafluoroethane and Supercritical CO2", Ind. Eng. Chem. Res., vol. 46, No. 1 (2007) pp. 22-28.

*Primary Examiner* — Heidi Reese
(74) *Attorney, Agent, or Firm* — Millen White Zelano and Branigan, PC; John Sopp; Anthony Zelano

(57) ABSTRACT

The present invention relates to the use of fluorinated surfactants of formula (I) in pesticides.

16 Claims, 3 Drawing Sheets

FLUOROSURFACTANTS IN PESTICIDES

Figures 1A, 1B:
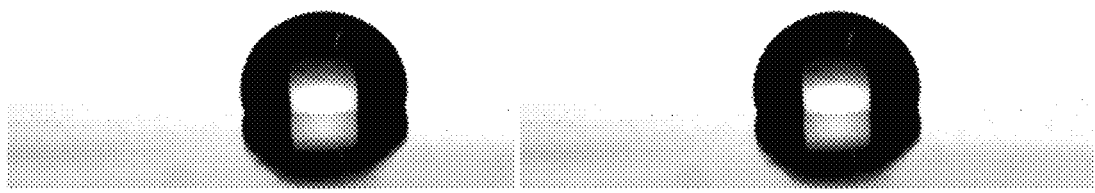
Figures 1C, 1D:
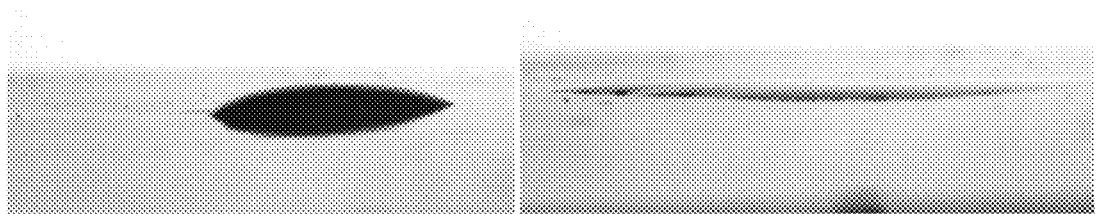
Figures 1E, 1F:
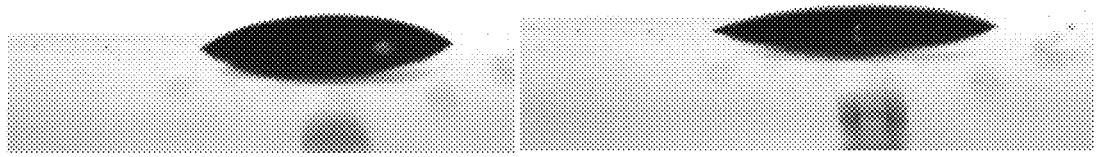
Figures 1G, 1H:
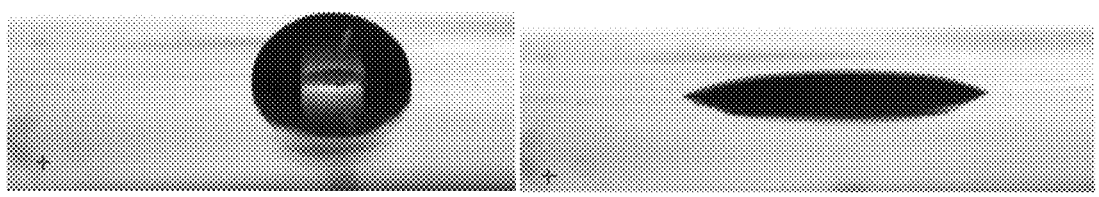
Figures 1I, 1J:
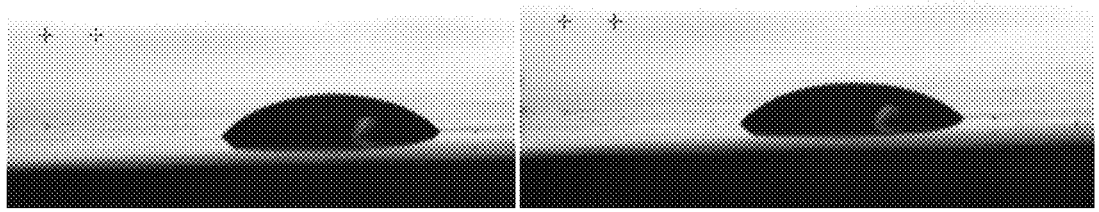
Figure 2:
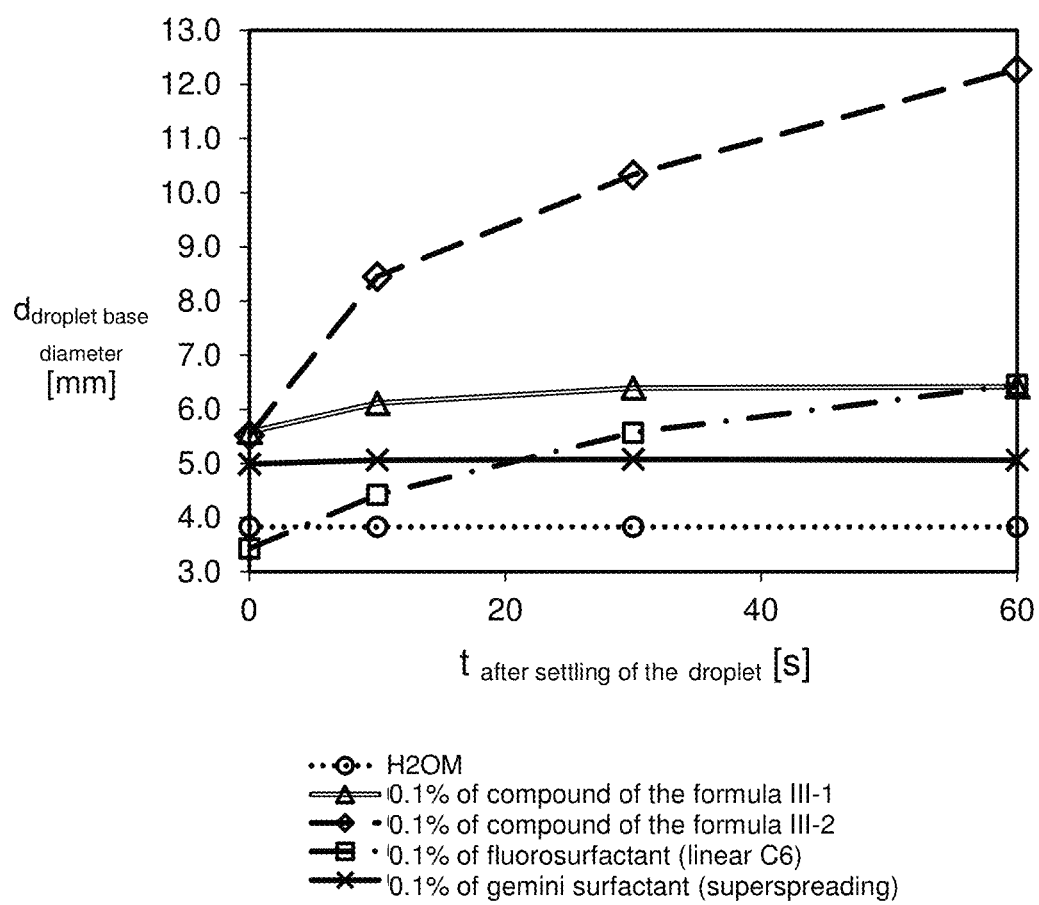
Figures 3A, 3B:
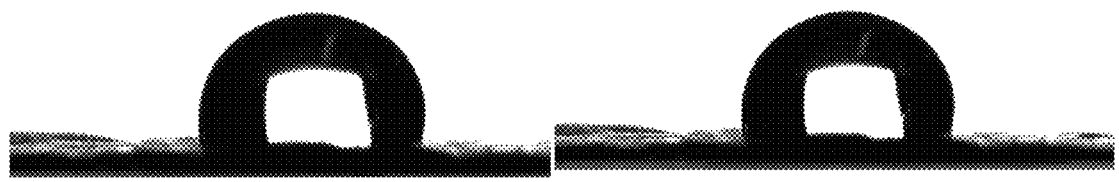
Figures 3C, 3D:
Figures 3E, 3F:
Figures 3G, 3H:
Figures 3I, 3J:
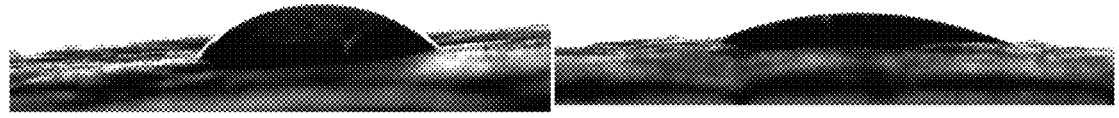

The present invention relates to the use of fluorosurfactants of the formula (I) in pesticides.

For the preparation of pesticides, in particular in crop protection, so-called adjuvants are employed besides the regular active compounds. Adjuvants here are in accordance with ASTM E 1519 substances which are added to the pesticide active compounds in order to improve the action of pesticides and/or their physical properties. Adjuvants are divided into two main functional classes:

A. Adjuvants which maintain or improve the efficacy of the pesticide. These include, in particular, substances which result in the following effects: improved wetting properties (for example superspreading), more efficient adsorption and uptake of the active compound (penetration), moistening action, droplet size as a function of spray pressure, etc.

B. Adjuvants which influence the practical use. Mention should be made here primarily of the following: emulsifiers, pH modifiers, foam formers, antifoams, substances for reducing the spray excess (drift).

Surfactants are one of the most important classes within the adjuvants and are used in both areas of application. They primarily fulfil the functions for improved wetting of the surface and thus ensure more efficient penetration of the active compound. Furthermore, they function as solubility promoters in the form of emulsifiers and dispersion additives in order to homogenise the active compounds, which are usually non-polar, in aqueous solutions. As emulsifiers, they are employed in various formulations: wettable powders (WP), oil-in-water or water-in-oil emulsions (EW or EO), suspensions (SC), suspoemulsions (SE), emulsifiable concentrates (EC) or also granules or water-dispersible granules.

Since plant surfaces are frequently characterised by an epicuticular hydrophobic wax layer and various leaf morphologies (for example hairs, wax crystals) are evident, they are only wetted poorly by aqueous active-compound solutions. This greatly restricts the uptake of the active compound by the plants due to two essential issues: firstly, "dripping-off" of the aqueous active-compound solution occurs during the spraying process, so that there is insufficient contact time with the leaf surface in order to take up the active compound. Secondly, the adhering droplets of the spray solution form only very small contact areas on the leaf surface, which restricts the uptake kinetics of the active compound. The addition of surfactants enables the wetting properties to be modified and the efficiency thus to be greatly improved. In the optimum case, the surfactant causes a great reduction in the surface tension in order to wet the plant surface covered with wax and in addition exhibits superspreading wetting behaviour. Adjuvants, their classification, properties and modes of action area described in Winnacker-Küchler, "Chemische Technologie" [Chemical Technology], Volume 7, C. Hanser-Verlag Munich, 4th Edition 1986.

To date, two main material classes of surfactants or surfactant mixtures have been employed as adjuvants: surfactants based on hydrocarbons and siloxanes. Thus, patent CA 2230769 describes the use of non-ionic siloxane surfactants, which results in a larger wetting area of the spray solution and thus in more efficient efficacy of the pesticide employed. Furthermore, WO 2010/003889 discusses the increased efficiency of active compounds based on the addition of ethoxylated sorbitol surfactants. Further uses of surfactants as adjuvants are described, inter alia, in Conference Proceedings 9th International Symposium on Adjuvants for Agrochemicals, ISAA 2010.

Previous surfactants as adjuvants, in particular non-ionic silicone, and hydrocarbon surfactants, exhibit only inadequate wetting properties on surfaces relevant for the use of pesticides, since their potential for reducing the surface tension in water is restricted to >20 mN/m. In addition, only few of these surfactants exhibit superspreading properties and tend towards increased foam formation in pesticide formulations, which is undesired owing to the poorer processing. In addition, classical fluorosurfactants are based on long-chain perfluorinated chains, which have proven highly bioaccumulative and toxic and have an inhalation-toxic action on spraying, meaning that extensive protective measures for the operating personnel become necessary.

Fluorosurfactants which are used as adjuvants in pesticides have only been described with little detail in the literature. M. Pisante et al. (J. Pestic. Sci., 32(1), 2007, 16-23) discuss evident advantages with respect to wetting and the associated more efficient uptake of active compound.

Specific applications of sulfosuccinates and/or sulfotricarballylates having various fluorinated side chains are described in U.S. Pat. No. 4,968,599 and U.S. Pat. No. 4,988,610 and U.S. Pat. No. 6,890,608 and in A. R. Pitt et al., Colloids and Surfaces A: Physicochemical and Engineering Aspects, 1996, 114, 321-335; A. R. Pitt, Progr. Colloid Polym. Sci, 1997, 103, 307-317 and Z.-T. Liu et al., Ind. Eng. Chem. Res. 2007, 46, 22-28. Further fluorosurfactants, in particular succinates and tricarballylates containing fluorinated alkyl groups, are described in WO 2009/149807, WO 2010/003567, WO 2010/149262, WO 2011/082770 and WO 2012/084118.

It has now been found that the use of certain fluorosurfactants as adjuvants in pesticides avoids the disadvantages of the prior art. Pesticides here include both pest-control agents in general and also crop-protection agents. The use of the compounds according to the invention is particularly advantageous in crop-protection agents. The terms pesticides or crop-protection agents and pest-control agents in the present invention are applied to formulations which comprise the corresponding active compounds for pest control or for crop protection and additives and/or solvents.

The present invention relates firstly to the use of compounds of the formula (I) in pesticides:

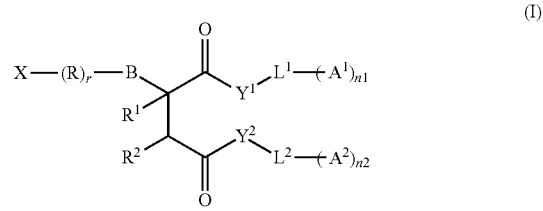

where
X is a hydrophilic group,
R is linear or branched alkylene, where one or more non-adjacent C atoms may be replaced by O, S, and/or N,
r is 0 or 1,
B is a single bond, O, NH, NR', $CH_2$, C(O)—O, S, $CH_2$—O, O—C(O), O—C(O)—O, N—C(O), C(O)—N, O—C(O)—N, N—C(O)—N, $SiR'_2$—, $SiR'_2$—O, O—$SO_2$ or $SO_2$—O, where R' is linear or branched alkyl,
$R^1$ and $R^2$, independently of one another, are hydrogen or —$CH_2$—$COY^3$-$L^3$-$(A^3)_{n3}$,
$Y^1$, $Y^2$ and $Y^3$, independently of one another, are O, S or N, $L^1$, $L^2$ and $L^3$, independently of one another, are linear or branched alkylene, where one or more non-adjacent C atoms may be replaced by O, S, and/or N, $A^1$, $A^2$ and $A^3$, independently of one another, are hydrogen or a group of the structure $-Z^i(CR^3R^4)_{mi}Rf^i$, where i=1, 2 or 3, $Z^i$ is O, S or N and is bonded to a C atom of $L^i$ or is a single bond, $R^3$ and $R^4$, independently of one another, are hydrogen or an alkyl group, $Rf^i$ is a fluorine-containing radical, n1, n2 and n3, independently of one another, are 1-6, m1, m2 and m3, independently of one another, are 0-5 and the compounds of the formula (I) contain at least one $Rf^i$ group.

The fluorosurfactants of the formula (I) used are preferably built up from a plurality of short-chain perfluoroalkyl groups with anionic, cationic, non-ionic and amphoteric groups. The compounds according to the invention are distinguished by improved properties on use as adjuvants.

In particular, branched fluorosurfactants containing short-chain perfluoroalkyl chains can lead to an improved eco-toxicological profile, since such compounds are non-toxic and do not exhibit bioaccumulation or inhalative toxicity. Personal protective measures during processing which are attributable to the toxicity of the surfactants are thus superfluous.

On use in pesticides, in particular in crop-protection agents, the compounds of the formula (I) can improve both the efficacy of the active compounds and/or also act, for example, as dispersant, emulsion stabiliser and/or foam inhibitor.

The use of the fluorosufactants according to the invention enables, in particular, the wetting properties of pesticides, in particular of crop-protection agents, to be significantly improved. By means of the fluorosurfactants of the formula (I), the surface tension in water can be reduced to below 20 mN/m, which results in a significant improvement in the wetting properties on the leaf surface compared with the siloxane- and hydrocarbon-based surfactants employed to date.

In addition, some of the branched fluorosurfactants exhibit superspreading wetting properties. This results in higher efficiency of the active compounds used in the pesticides, since both drift is reduced and also the contact area for the uptake of the active compound is increased. Due to the enlarged surface, a spray film of the pesticide also dries more rapidly, the active compound is consequently concentrated homogeneously on the leaf and cannot drip off the leaf so quickly.

The fluorosurfactants described here also improve numerous other properties. Thus, reduced foam formation in water can be demonstrated in the Ross-Miles test and in the Tego foam test. This is advantageous, in particular, in the preparation of spray solutions.

Fluorosurfactants of the formula (I) can be employed in all pesticides, both for crop protection and also generally for pest control. These compounds can advantageously be employed, in particular, in crop-protection agents, for example in herbicides, insecticides, fungicides, algicides, aphicides, nematicides, acaricides, molluscicides, bactericides, virucides, rodenticides or plant-growth regulators. The compounds of the formula (I) are also suitable for use in further crop-protection agents, such as, for example, in agents for the grafting of woody plants, agents for preventing damage by wildlife, agents for soil decontamination and dressings for the treatment of seed and plant material.

Compounds of the formula (I) are usually added to liquid pesticide formulations which are applied by means of spray methods. However, use in other pesticide formulations, such as wettable powders (WP), oil-in-water or water-in-oil emulsions (EW or EO), suspensions (SC), suspoemulsions (SE), emulsifiable concentrates (EC) or also granules or water-dispersible granules, is also possible. Use of the compounds of the formula (I) in formulations of crop-protection agents which are applied by spray methods in the cultivation of crop or ornamental plants is particularly advantageous.

Preferred compounds of the formula (I) are those in which two or three $Rf^i$ groups are present. However, compounds containing at least four $Rf^i$ groups are also possible, preferably containing four, six or nine $Rf^i$ groups.

The fluorinated groups $Rf^i$ used are preferably branched or unbranched, fluorine-containing alkyl radicals, in particular perfluorinated alkyl radicals.

Particular preference is given to fluorine-containing alkyl radicals having 1 to 10, preferably 1 to 6, in particular 1 to 4, C atoms. Especial preference is given to the use of perfluorinated $Rf^i$ groups having 1 to 6, in particular 1 to 4, C atoms. $Rf^1$, $Rf^2$ and $Rf^3$ preferably have the same meaning.

$R^1$ and $R^2$ are preferably not simultaneously $-CH_2-COY^3-L^3-(A^3)_{n3}$.

Preferred compounds of the formula (I) are in addition those in which $Y^1$, $Y^2$ and $Y^3$ preferably denote O or N, in particular O. $Y^1$ and $Y^2$ or $Y^1$, $Y^2$ and $Y^3$ have the same meaning.

The groups $Rf^i$ are bonded to a group $L^1$, $L^2$ or $L^3$ via a $-Z^i(CR^3R^4)_{mi}$ group. $Z^i$ here preferably stands for O or N, in particular for O. Preference is given to compounds in which all $Z^i$ are identical.

Preferred compounds of the formula (I) are those in which n1, n2 and n3 preferably, independently of one another, 0-4, in particular 1 or 2.

Preferred compounds of the formula (I) are also those in which m1, m2 and m3 are preferably, independently of one another, 0-4, in particular 1-4.

Preferred compounds of the formula (I) are also those in which $R^3$ and $R^4$ independently of one another, hydrogen or an alkyl group having 1 to 6 atoms, in particular 1-4 C atoms. $R^3$ and $R^4$ preferably stand, independently of one another, for hydrogen or an unbranched C1-C3-alkyl group. Preference is given to compounds in which $R^3$ or $R^4$ is equal to hydrogen, m1, m2 and m3 preferably stand, independently of one another, for 1-3. Preference is given to compounds in which all $Z^i$, $R^3$, $R^4$ and mi in each case have the same meaning.

$L^1$, $L^2$ and $L^3$ can preferably, independently of one another, be linear or branched alkylene having 1 to 10 C atoms. In particular, $L^1$, $L^2$ and $L^3$ are, independently of one another, linear or branched alkylene having 3 to 8 C atoms. One or more non-adjacent C atoms of the groups $L^1$, $L^2$ and $L^3$ may preferably be replaced by O or N, preferably by O. In a preferred variant of the invention, $L^1$ and $L^2$ are identical. If $L^3$ is also present, $L^1$ and $L^2$ or $L^1$ and $L^3$ or $L^2$ and $L^3$ may preferably be identical. In a particularly preferred variant of the invention, all groups $L^1$, $L^2$ and $L^3$ are identical.

Particular preference is given to compounds of the formula (I) in which at least one group $L^i=-(CR^5R^6)_{ci}(CR^7R^8)_{c'i})_{di}-$, where the respective indices ci and c'i are, independently of one another, 0-10 and di is 0-5, $R^5$ to $R^8$ are, independently of one another, hydrogen or a branched or unbranched alkyl group and ci and c'i are not simultaneously 0.

Especial preference is given to compounds of the formula (I) in which, in at least one group $L^i$, the group $R^5$ is an alkyl group having 1 to 6 C atoms, in particular 1-4 C atoms, and the groups $R^6$ and $R^7$ and $R^8$ are hydrogen.

Preference is furthermore also given to compounds of the formula (I) in which $R^7$ is an alkyl group having 1 to 6 C atoms, in particular 1-4 C atoms, and the groups $R^5$ and $R^6$ and $R^8$ are hydrogen.

In the compounds of the formula (I), the group R preferably stands for linear or branched alkylene having 1 to 12 carbon atoms, in particular having 1 to 4 carbon atoms. One or more non-adjacent C atoms may preferably be replaced by O or S, preferably O.

In the compounds of the formula (I) according to the invention, r can preferably be equal to 0.

Preference is furthermore given to compounds of the formula (I) in which B is a single bond, O, S, C(O)—O or O—C(O), in particular a single bond.

Particularly advantageous compounds of the formula (I) are those in which one or more of the variables Rf, $Y^1$, $Z^1$, U, $R^1$ to $R^8$, ci, c'i, di, ni, mi, R, r and B have the preferred meanings, in particular compounds in which the said variables have the particularly preferred meanings. Particularly advantageous compounds of the formula (I) are those in which all said variables have the preferred meanings, in particular the particularly preferred meanings.

In the compounds of the formula (I) according to the invention, X is a hydrophilic group, preferably an anionic, cationic, nonionic or amphoteric group.

A preferred anionic group X can be selected from —COO$^-$, —SO$_3^-$, —OSO$_3^-$, —PO$_3^{2-}$, —OPO$_3^{2-}$, —(OCH$_2$CH$_2$)$_s$—O—(CH$_2$)$_t$—COO$^-$, —(OCH$_2$CH$_2$)$_s$—O—(CH$_2$)$_t$—SO$_3^-$, —(OCH$_2$CH$_2$)$_s$—O—(CH$_2$)$_t$—OSO$_3^-$, —(OCH$_2$CH$_2$)$_s$—O—(CH$_2$)$_t$—PO$_3^{2-}$, —(OCH$_2$CH$_2$)$_s$—O—(CH$_2$)$_t$—OPO$_3^{2-}$ or from the formulae A to C,

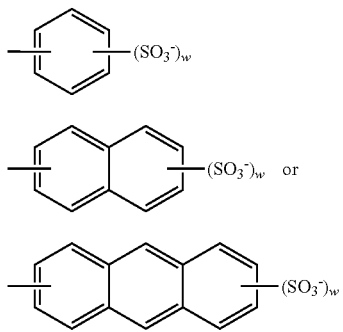

where s stands for an integer from the range from 1 to 1000, t stands for an integer selected from 1, 2, 3 or 4 and w stands for an integer selected from 1, 2 or 3.

The preferred anionic groups here include, in particular, —COO$^-$, —SO$_3^-$, —OSO$_3^-$, —PO$_3^{2-}$, —OPO$_3^{2-}$, the sub-formula A, and —(OCH$_2$CH$_2$)$_s$—O—(CH$_2$)$_t$—COO$^-$, —(OCH$_2$CH$_2$)$_s$—O—(CH$_2$)$_t$—SO$_3^-$ and —(OCH$_2$CH$_2$)$_s$—O—(CH$_2$)$_t$—OSO$_3^-$, where each individual one of these groups may be preferred per se.

The very particularly preferred anionic groups here include —SO$_3^-$, —OSO$_3^-$, —PO$_3^{2-}$ or OPO$_3^{2-}$. Especial preference is given to a sulfonate group —SO$_3^-$.

The preferred counterion for anionic groups X is a monovalent cation, in particular H$^+$, an alkali metal cation or NR$_4^+$, where R is H or C1-C6-alkyl and all R may be identical or different. Particular preference is given to Na$^-$, K$^+$ and NH$_4^+$ especially preferably Na$^+$.

A preferred cationic group X can be selected from —NR$^1$R$^2$R$^{3+}$Z$^-$, —PR$^1$R$^2$R$^{3+}$Z$^-$,

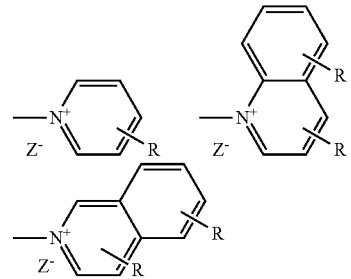

where R stands for H or C1-4-alkyl in any desired position,
Z$^-$ stands for Cl$^-$, Br$^-$, I$^-$, CH$_3$SO$_3^-$, CF$_3$SO$_3^-$, CH$_3$PhSO$_3^-$, PhSO$_3^-$
R$^1$, R$^2$ and R$^3$ each stand, independently of one another, for H, C$_{1-30}$-alkyl, Ar or —CH$_2$Ar and
Ar stands for an unsubstituted or mono- or polysubstituted aromatic ring or condensed ring systems having 6 to 18 C atoms in which, in addition, one or two CH groups may be replaced by N.

The preferred cationic groups here include, in particular, —NR$^1$R$^2$R$^{3+}$Z and

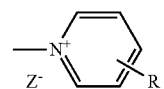

where each individual one of these groups may be preferred per se.

A preferred nonionic group can be selected from linear or branched alkyl, where one or more non-adjacent C atoms may be replaced by O, S, and/or N, —OH, —SH, —O-(glycoside)$_o$, —S-(glycoside)$_o$, —OCH$_2$—CHOH—CH$_2$—OH, —OCH$_2$Ar(—NCO)$_p$, —OAr(—NCO)$_p$, —CR═CH$_2$, —OCOCR═CH$_2$, amine oxide

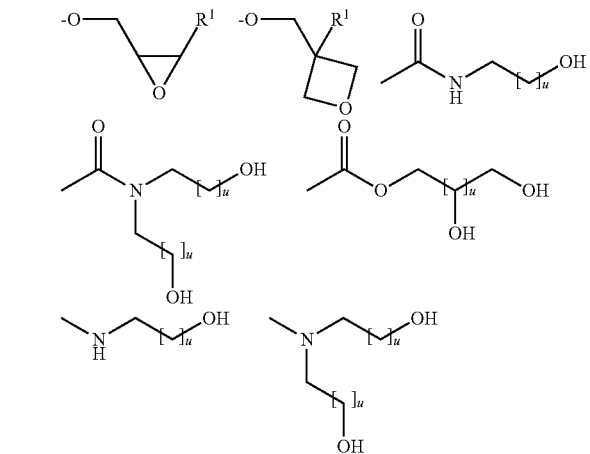

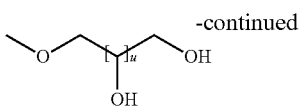

u stands for an integer from the range from 1 to 6, preferably 1 to 4,
stands for an integer from the range from 1 to 10,
p stands for 1 or 2,
$R^1$, $R^2$ and $R^3$ each stand, independently of one another, for $C_{1-30}$-alkyl, Ar or —$CH_2$Ar, preferably $C_{1-20}$-alkyl, and
Ar stands for an unsubstituted, mono- or polysubstituted aromatic ring or condensed ring systems having 6 to 18 C atoms in which, in addition, one or two CH groups may be replaced by C=O, and,
glycoside stands for an etherified carbohydrate, preferably for a mono- di-, tri- or oligoglucoside,
and R stands for H or methyl.

The preferred nonionic groups here include, in particular, linear or branched alkyl, where one or more non-adjacent C atoms may be replaced by O, S and/or N, —OH, —OCOCR=$CH_2$ and —O-(glycoside)$_o$.

If X=alkyl, where one or more non-adjacent C atoms have been replaced by O, S and/or N, it is then preferably equal to R-(B-A)$_m$-, where
R=H or $C_{1-4}$-alkyl, in particular H or $CH_3$, A=linear or branched alkylene, preferably having 1 to 10 carbon atoms, in particular having 1 to 4 carbon atoms, B=O or S, preferably O, and m=an integer preferably from the range from 1 to 100, particularly preferably 1 to 30.

The nonionic group X is particularly preferably the R—(O—$CH_2$CHR)$_m$— group, where m=an integer from the range from 1 to 100, preferably 1 to 30, in particular 1-15, and R=H or $C_{1-4}$-alkyl, in particular H or $CH_3$. R-(B-A)$_m$- is particularly preferably a polyethylene or polypropylene glycol unit.

A preferred amphoteric group can be selected from the functional groups of the acetyldiamines, the N-alkylamino acids, the betaines or corresponding derivatives, in particular selected from:

Particularly preferred compounds according to the invention are those which contain one of the preferred anionic groups X, the preferred nonionic groups or the preferred zwitterionic groups as hydrophilic group X.

Especial preference is given to compounds which contain the groups —$SO_3$, —$OSO_3^-$, —$PO_3^{2-}$ or $OPO_3^{2-}$, polyethylene glycol or polypropylene glycol, betaines, or sulfobetaines, in particular —$SO_3^-$. Preferred counterions here are $Na^+$, $K^+$ and $NH_4^-$ in particular $Na^+$.

Compounds of the formula (I) in which X is an anionic group, in particular —$SO_3^-$, and one or more of the variables $Rf^i$, $Y^i$, $Z^i$, $L^i$, $R^1$ to $R^8$, ci, c'i, di, ni, mi, R, r and B have the preferred meanings described, in particular compounds in which the said variables have the particularly preferred meanings, are particularly advantageously employed in pesticides. Preferred compounds here are, in particular, compounds in which all variables have the preferred meanings, especially the particularly preferred meanings.

In an embodiment of the invention, the compounds of the formula (I) can be in the form of mixtures in which the individual compounds have different meanings for the variables, in particular for $A^i$, $Rf^i$, $Y^i$, $Z^i$, $L^i$, $R^1$ to $R^8$, ci, c'i, di and mi.

In a particularly preferred group of compounds of the formula (I), $R^1$ and $R^2$ for hydrogen and $A^1$ and $A^2$ stand for a —$Z^i(CR^3R^4)_{mi}Rf^i$ group. These compounds are represented by formula (II). Particular preference is given to compounds of the formula (II) where $Y^1$, $Y^2$, $Z^1$ and $Z^2$ are equal to O.

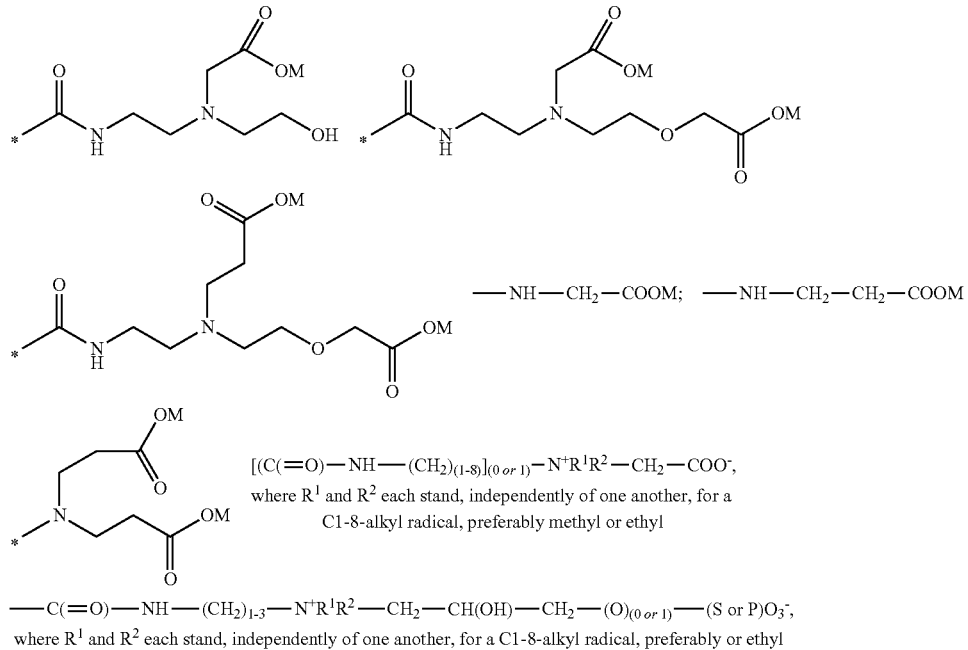

In another preferred group of compounds of the formula (I), $R^1$ stands for H, $R^2$ stands for $-CH_2-COY^3-L^3-(A^3)_{n3}$ and $A^1$, $A^2$ and $A^3$ stand for a $-Z^i(CR^3R^4)_{mi}Rf^i$ group. These compounds are represented by formula (III). Particular preference is given to compounds of the formula (III) where $Y^1$, $Y^2$, $Z^1$ and $Z^2$ are equal to O.

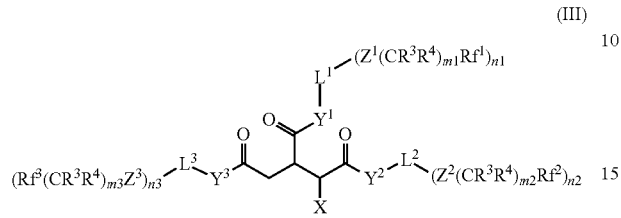

(III)

In a further preferred group of compounds of the formula (I), $R^1$ stands for $-CH_2-COY^3-L^3-(A^3)_{n3}$, $R^2$ stands for hydrogen and $A^1$, $A^2$ and $A^3$ stand for a $-Z^i(CR^3R^4)_{mi}Rf^i$ group. These compounds are represented by formula (IV). Particular preference is given to compounds of the formula (IV) where $Y^1$, $Y^2$, $Y^3$, $Z^1$, $Z^2$ and $Z^3$ are equal to O.

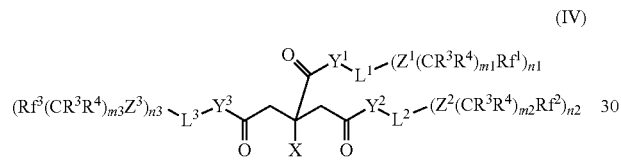

(IV)

Particularly preferred compounds according to the invention are compounds of the formulae (II), (III) and (IV) in which X is an anionic group. Especial preference is given to compounds of the formulae (II), (III) and (IV) which contain the groups $-SO_3^-$, $-OSO_3^-$, $-PO_3^{2-}$ or $OPO_3^{2-}$, in particular $-SO_3^-$. Preferred counterions here are $Na^+$, $K^+$ and $NH_4^+$, in particular $Na^+$.

In the formulae (II), (III) and (IV), $L^1$, $L^2$ and $L^3$ have the general and preferred meanings given for the formula (I). $L^1$, $L^2$ and $L^3$ are preferably, independently of one another, equal to linear or branched C1-C10-alkylene, in particular linear or branched C3-C8-alkylene, preferably equal to linear or branched C3-C6-alkylene. Especial preference is given to compounds of the formulae (II), (III) and (IV) in which all L are identical.

In addition, preference is given to compounds of the formulae (II), (III) and (IV) containing perfluorinated groups $Rf^i$ having 1 to 4 C atoms. $Rf^1$, $Rf^2$ and $Rf^3$ preferably have the same meaning.

In the formulae (II), (III) and (IV), n1, n2 and n3 are preferably, independently of one another, 1 or 2. m1, m2 and m3 are preferably, independently of one another, 1-4.

Preferred compounds of the formulae (II), (III) and (IV) are also those in which $R^3$ and $R^4$ are, independently of one another, hydrogen or an alkyl group having 1 to 3 C atoms.

In a preferred variant, $R^3$ and $R^4$ are identical. Preference is furthermore given to compounds in which $R^3$ or $R^4$ are equal to hydrogen and m1, m2 m3 are equal to 1-3.

Preference is given to compounds in which all $Rf^i$, $R^3$, $R^4$, ni and mi in each case have the same meaning.

Particular preference is given to compounds of the formulae (II), (III) and (IV) in which all variables have the preferred meanings, in particular the particularly preferred meanings.

Examples of compounds of the formula (I) whose use in pesticides is particularly advantageous are compounds of the formulae (I-1) and (III-2):

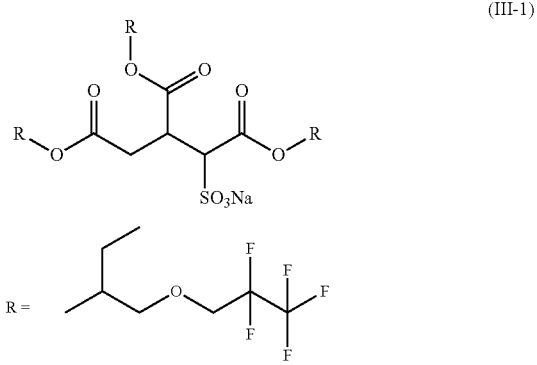

(III-1)

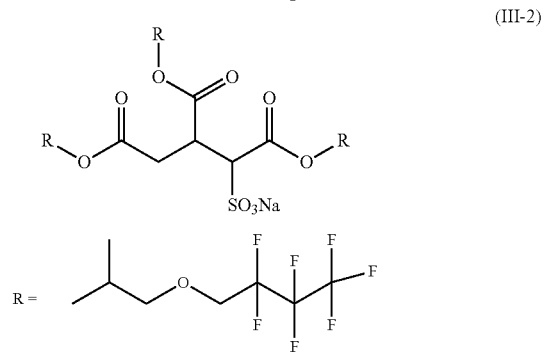

(III-2)

The compounds of the formula (I) according to the invention may also be in the form of isomer mixtures (constitutional and/or configurational isomer mixtures). In particular, diastereomer and/or enantiomer mixtures are possible.

The compounds of the formula (I) according to the invention can preferably be prepared by esterification of maleic acid and aconitic acid or anhydrides or acid chlorides thereof using one or more alcohols of the formula (IV)

(V)

and subsequent addition onto the double bond in order to introduce the $X-(R)_r$-B group. The compounds according to the invention can also preferably be prepared by esterification of hydroxysuccinic acid and citric acid using one or more alcohols of the formula (V) and subsequent functionalisation of the hydroxyl groups in order to introduce the $X-(R)_r$-B group.

L and A in the formula (V) have the meaning described for $L^1$, $L^2$ and $L^3$ and $A^1$, $A^2$ and $A^3$ respectively in formula (I), in particular also the preferred meanings. The alcohols of the formula (V) may contain one or more Rf groups.

The alcohols used are commercially available and/or their preparation is familiar to the person skilled in the art (for example DE 10 2009 030 846 A1; Heilmann et al. J. Fluorine Chem. 1992, 59, 387; Janulis et al. U.S. Pat. No. 5,157,159 (1992); Carbohydrate Research 1991, 219, 33).

The synthesis of succinates or tricarballylates according to the invention is preferably carried out in a two-step synthesis via the corresponding maleates or hydroxysuccinates or the corresponding aconitic or citric acid esters. These syntheses are described in WO 2010/149262, WO 2011/082770 and WO 2012/084118. The disclosures in the references cited hereby expressly also belong to the disclosure content of the present application.

The invention furthermore relates to pesticides comprising at least one compound of the formula (I). In particular, the preferred compounds described hereinabove, especially the compounds of the formulae (II) to (IV), can be used here. The pesticides according to the invention may comprise one or more of the said fluorosurfactants.

The pesticides can be both pest-control agents in general and also crop-protection agents, such as, for example, herbicides, insecticides, fungicides, algicides, aphicides, nematicides, acaricides, molluscicides, bactericides, virucides, rodenticides, plant-growth regulators, agents for grafting woody plants, agents for preventing damage by wildlife, agents for soil decontamination and dressings for the treatment of seed and plant material.

The pesticides may be present in various formulations, for example as wettable powders (WP), oil-in-water or water-in-oil emulsions (EW or EO), suspensions (SC), suspoemulsions (SE), emulsifiable concentrates (EC) or also granules or water-dispersible granules. In particular, crop-protection agents which are applied by spraying methods in the cultivation of crop or ornamental plants are suitable.

Besides the fluorosurfactants of the formula (I), pesticides according to the invention may furthermore also comprise surfactants, such as, for example, silicone surfactants based on polydimethylsiloxanes, functional trisiloxanes, gemini hydrocarbon surfactants and other hydrocarbon surfactants. The compounds of the formula (I) can preferably be used in mixtures with one or more of the compounds of the formulae (VI) to (X).

The pesticides preferably comprise at least one compound of the formula (VI)

$$(RF\text{-}(spacer)_m)_n M \quad \text{(VI)}$$

where
RF is a fluorine-containing group,
spacer is a single bond or an organic functional carbon chain,
n is $\geq 1$,
m=0-1 and
M is an anionic, cationic, amphoteric or non-ionic group.

Preferred compounds of the formula (VI) are those in which RF is a perfluorinated alkyl group having at least two C atoms, preferably three C atoms, in particular four C atoms. Especial preference is given to substances which contain a perfluorinated C6 chain connected to an ethyl radical.

The spacer group can preferably be an organic functional hydrocarbon chain, for example a linear or branched alkylene, where one or more non-adjacent C atoms may be replaced by O, S and/or N.

Preference is furthermore given to compounds of the formula (VI) in which the (RF-(spacer)$_m$)$_n$- group is equal to $C_nF_{2n'+1}$—, $C_nF_{2n'+1}$—$CH_2CH_2$—, $C_nF_{2n'+1}$—$OCF_2CF_2$—, $C_nF_{2n'+1}$—$OC_6H_4$—, $C_nF_{2n'+1}$—$C(O)NH(CH_2)_3N$=, $C_nF_{2n'+1}$—$SO_2NH(CH_2)_3N$=, $CF_3CCl_2(CF_2CFCl)_{n-1}$—$CF_2$— or $C_8F_{17}CH_2CH_2Si(CH_3)_2$—, where n'=4-12. Particular preference is given to the $C_nF_{2n'+1}$—$CH_2CH_2$— group where n'=4-8.

Preferred anionic groups M are —OPOO$^-$, —COO$^-$, —SO$_3^-$, —OSO$_3^-$, —OP(O)(O$^-$)O— and —OP(O)O$_2^{2-}$. The counterions used here are preferably H$^+$, Na$^+$, K$^+$, Li$^+$ or NH$_4^+$.

Particular preference is given to compounds of the formula (VI-a)

where RF=CF$_3$—(CF$_2$)$_n$-spacer-, where n=0-12, and cation=Na, K, Li, NH$_4$. Spacer has the meaning indicated above.

Preferred cationic groups M are —NR$_3^+$ groups where R=C1-C4 alkyl.

Preferred amphoteric groups M are —NR$_2^+$—(CH$_2$)$_y$—COO$^-$ groups where R=C1-C4 alkyl and y=1-3, preferably y=1.

Preferred nonionic groups M are (OCH$_2$CH$_2$)$_n$—OR and —(OCH$_2$(CH$_3$)CH$_2$)$_n$—OR where n=4-40 and R=H or C1-C4 alkyl.

Preferred compounds of the formula (VI) are, in particular, compounds in which all variables have the preferred meanings. Preference is given to anionic fluorosurfactants, for example based on phosphoric acid, carboxyl and sulfonic acid groups. Especial preference is given to compounds of the formula (VI) in which M is an anionic group and the (RF-(spacer)$_m$)$_n$- group is equal to $C_nF_{2n'+1}$—$CH_2CH_2$—, where n=4-8. Particularly preferred compounds here are phosphoric acid esters of the formula (VI-a), especially those with NH$_4^+$ as counterion.

The compounds of the formula (II) employed in the pesticides according to the invention are known to the person skilled in the art. They can be prepared analogously to known synthetic processes or are commercially available. The phosphoric acid esters which are particularly preferably used are available, for example, from Chemguard under the trade name Chemguard®, for example Chemguard® S760-P.

Preferred pesticides of the invention comprise the preferred compounds of the formula (I) described above and the preferred compounds of the formula (VI) described above.

Especial preference is given to pesticides comprising fluorosurfactants of the formulae (II), (III) and (IV), in particular of the formulae (III-1) and (III-2), in combination with the said preferred phosphoric acid esters.

Besides the compounds of the formula (I), the pesticides according to the invention may also comprise at least one sulfosuccinate, preferably of the formula (VII),

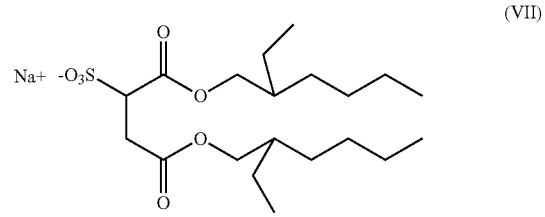

The pesticides may also comprise at least one functional polymer based on polymethylsiloxane, preferably of the formula (VIII),

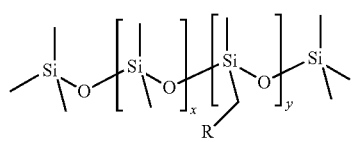
(VIII)

where x=1-500, y=1-500 and R=phenyl, methyl or —(O—C$_2$H$_3$R')$_{n''}$—OR'', where n''=1-1000, R'=linear and branched alkyl radical and R''=linear and branched alkyl radicals.

The pesticides may also comprise at least one trisiloxane derivative, preferably of the formula (IX), $$M_2D'(E_{n'''}P) \qquad (IX)$$

where M=(CH$_3$)$_3$SiO—, D'=Si(R'''), E=—OCH$_2$CH$_2$, n'''=5-40 and P=—OH, —OMe, or —OAc, where R'''=linear and/or branched alkyl chain.

Especial preference is given to the following compound

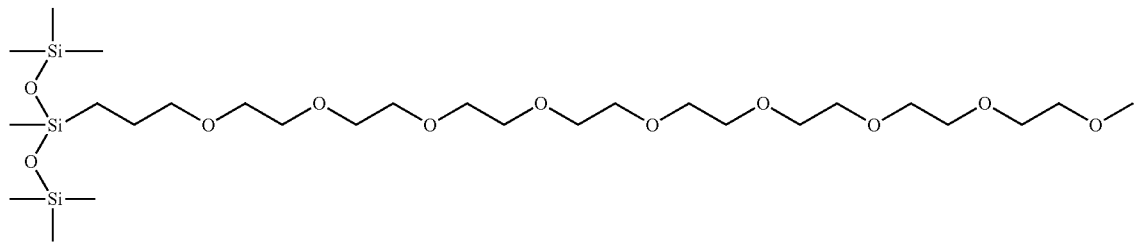

The pesticides according to the invention may also comprise at least one gemini surfactant, where two identical or different amphiphilic groups built up from structures of conventional surfactants are connected by a spacer. Especial preference is given, for example, to diacetylene derivatives of the formula (X)

(X)

where n=1-100.

If mixtures of the compounds of the formula (I) with other surfactants are used, these mixtures comprise one or more of the compounds of the formula (I) and one or more of the compounds of the formulae (II) to (X) preferably in the ratio of 70/30 to 90/10, in particular in the ratio of 80/20 to 85/15 ratio).

The content of the compounds of the formula (I) or the content of mixtures thereof, also with the said surfactants of the formulae (VI)-(X), is usually 0.01-1.0% by weight, preferably 0.05-0.5, in particular 0.05-0.2% by weight, based on the entire pesticide formulation. 0.1% by weight formulations can particularly preferably be used.

Pesticides which comprise the compounds according to the invention may comprise the water-soluble and/or water-insoluble active compounds known to the person skilled in the art, such as, for example, glyphosate, glufosinate, paraquat, hentazon, fomesafen, nicosulfuron, chlorsulfuron, butroxydim, thifensulfuron, aclonifen, permethrin, pyrethrin, disulfoton, armitraz, diazinon, metalazyl, inter alia.

Besides the compounds (I) or mixtures of these compounds with compounds of the formula (VI) and/or compounds of the formulae (VII) to (X), the crop-protection agents according to the invention may also comprise conventional solvents and/or additives, such as, for example, dyes, humectants, rheology modifiers, frost-protection agents, etc.

The complete disclosure content of all applications and publications mentioned above is incorporated into this application by way of reference. In the description and examples, percentages are percent by weight, unless indicated otherwise. The following examples explain the invention in greater detail without restricting the scope of protection.

EXAMPLES

Example 1: Synthesis of the Compound of the Formula (III-1)

The chain-extended alcohol is prepared from the starting materials 2,2,3,3,3-pentafluoropropan-1-ol (ABCR) and butylene carbonate (TCI) in accordance with patent application DE 10 2009 030 846 A1. This intermediate is esterified using aconitic acid (Alfa Aesar) by the synthetic procedure described and then sulfonated in the final reaction step by means of an aqueous sodium hydrogensulfite solution (Merck KGaA). The dynamic surface tension is determined by the method indicated and is 28.2 mN/m (100 ms, 0.1% by weight).

Example 2: Synthesis of the Compound of the Formula (III-2)

The chain-extended alcohol is prepared from the starting materials 2,2,3,3,4,4,4-heptafluorobutan-1-ol (ABCR) and propylene carbonate (Merck KGaA) in accordance with patent application DE 10 2009 030 846. This intermediate is esterified using aconitic acid by the synthetic procedure described and then sulfonated in the final reaction step by means of an aqueous sodium hydrogensulfite solution. The dynamic surface tension is determined by the method indicated and is 66.6 mN/m (100 ms, 0.1% by weight).

Example 3: Investigations into the Wetting on PTFE Film in Accordance with ASTM E2044 8 (Standard Test Method for Spreading of Liquid Agricultural Spray Mixtures)

Instrument: Krüss contact angle measuring instrument (DSA 100) Substrate: PTFE film from Goodfellow GmbH; measurement on the outside; (average roughness $R_M$=20-30 nm)

Measurement Method Employed:

In accordance with ASTM E2044, the droplet base diameter (d) of an aqueous surfactant solution (0.1% by weight surfactant concentration) on a PTFE film is determined after various times. In this method, a 20 μl droplet of the liquid is applied to the corresponding surface using a syringe through a PTFE capillary (type N44; d=0.776 mm) (separation of the capillary from the surface=5 mm). With the aid of a contact angle measuring instrument, the droplet base diameter is determined after 0 s; 10 s, 30 s and 60 s. The droplet base diameter is measured using a digital ruler (length in pixels) after a video recording of the wetting operation and can be converted to a length (in mm) by magnifying the capillary (the diameter of the capillary corresponds to a corresponding number of pixels at a certain magnification).

FIG. 1 shows the droplets of various aqueous surfactant solutions compared with pure water after 0 s and after 60 s. Significant advantages are evident in relation to the wetting behaviour, in particular for the compound of the formula (III-2). The solution of the compound of the formula (III-2) has the largest droplet base diameter after 60 s and exhibits superspreading behaviour on Teflon.

FIG. 2 shows the droplet base diameter as a function of the various residence times (t) on the PTFE film. Solutions comprising the compound of the formula (III-2) and the compound of the formula (III-1) exhibit a significantly greater droplet base diameter than all other surfactant solutions both after 0 and also after 10 s. This can probably be explained by very rapid wetting of the PTFE film.

Example 4: Investigations into the Wetting on Leaves of the Müller-Thurgau Grapevine (*Vitis vinifera*)

Instrument: Krüss contact angle measuring instrument (DSA 100) Substrate: leaves of the Müller-Thurgau grapevine; leaf section having a relatively homogeneous surface (top, leaf size~7×8 cm)

Measurement Method Employed:

The wetting behaviour of aqueous surfactant solutions (0.1% surfactant concentration) is investigated qualitatively on the surface of grape plant leaves using a contact angle measuring instrument. For this purpose, a homogeneous leaf section is fixed to a watch glass (d=12 cm) having convex curvature. This enables liquid droplets to be investigated irrespective of the other curvatures of the leaf surface. In order to investigate the wetting behaviour, a 5 μl droplet of liquid is applied to the leaf surface using a syringe through a PTFE capillary (type N44; d=0.776 mm). Since accurate contact angle measurements cannot be carried out on the very rough surface of the grape plants, the wetting behaviour is assessed qualitatively after 0 s and 10 s.

FIG. 3 shows the droplets of various aqueous surfactant solutions compared with pure water after 0 s and after 10 s on the grape leaf surfaces. The use of the branched fluorosurfactants of the formula (III-2) and of the formula (III-1) reduces the contact angle of the droplets significantly compared with water ($H_2O$). In addition, the compound of the formula (III-2) exhibits better wetting properties than all other surfactant solutions after 10 s in the qualitative investigation.

FIGURES

FIG. 1 shows the wetting of a PTFE film by various aqueous surfactant solutions compared with pure water after 0 s and after 60 s. The droplet base diameter d is indicated in each case.

FIG. 1*a*: $H_2O$; t=0 s: d=3.8 mm

FIG. 1*b*: $H_2O$; t=60 s: d=3.8 mm

FIG. 1*c:* 0.1% of the compound of the formula (III-2); t=0 s: d=5.5 mm

FIG. 1*d:* 0.1% of the compound of the formula (III-2); t=60 s: d=12.3 mm

FIG. 1*e:* 0.1% of the compound of the formula (III-1); t=0 s: d=5.6 mm

FIG. 1*f:* 0.1% of the compound of the formula (III-1); t=60 s: d=6.4 mm

FIG. 1*g:* 0.1% of fluorosurfactant (linear C6); t=0 s: d=3.4 mm

FIG. 1*h:* 0.1% of fluorosurfactant (linear C6); t=60 s: d=6.5 mm

FIG. 1*i:* 0.1% of gemini surfactant; t=0 s: d=5.0 mm

FIG. 1*j:* 0.1% of gemini surfactant; t=60 s: d=5.1 mm

FIG. 2 shows the droplet base diameter (V=20 μl; 0.1% surfactant concentration) on PTFE film after various residence times FIG. 3 shows the wetting of grape leaf surfaces by various aqueous surfactant solutions FIG. 3*a*: $H_2O$; droplet at t~0 s FIG. 3*b*: $H_2O$; droplet at t~10 s FIG. 3*c:* 0.1% of the compound of the formula (III-1); droplet at t~0 s FIG. 3*d:* 0.1% of the compound of the formula (III-1); droplet at t~10 s FIG. 3*e:* 0.1% of the compound of the formula (III-2); droplet at t~0 s FIG. 3*f:* 0.1% of the compound of the formula (III-2); droplet at t~10 s FIG. 3*g:* 0.1% of fluorosurfactant (linear C6); droplet at t~0 s FIG. 3*h:* 0.1% of fluorosurfactant (linear C6); droplet at t~10 s FIG. 3*i:* 0.1% of gemini surfactant; droplet at t~0 s FIG. 3*j:* 0.1% of gemini surfactant; droplet at t~10 s

The invention claimed is:

1. A pesticide and/or crop-protection agent formulation comprising a pesticide and/or crop-protection agent and at least one compound of the formula (I)

(I)

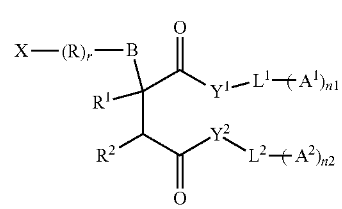

where X is an anionic group X selected from —COO—, —S0$_3$, —OSO$_3$, —PO32-, —OPO$_{32}$, —(OCH$_2$CH$_2$)s-O—(CH$_2$)—COO—, —(OCH$_2$CH$_2$)s-O—(CH$_2$)t-SO$_3$, —(OCH$_2$CH$_2$)s-O—(CH$_2$)t-OSO$_3$, —(OCH$_2$CH$_2$)s-O—(CH$_2$)t-PO3$^{2-}$—, —(OCH$_2$CH$_2$)s-O—(CH$_2$)t-OP0$_{32}$- or from the formulae A to C,

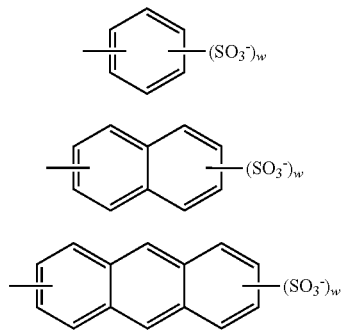

where s stands for an integer from the range from 1 to 1000, t stands for an integer selected from 1, 2, 3 or 4 and w stands for an integer selected from 1, 2 or 3, having a monovalent cation selected from H+, an alkali metal cation or NR$_1$+, where each R is, independently, H or C1-C6-alkyl;

as cationic group selected from —NRR$^2$R$^3$+Z, —PR$^1$R2R$^3$+Z—,

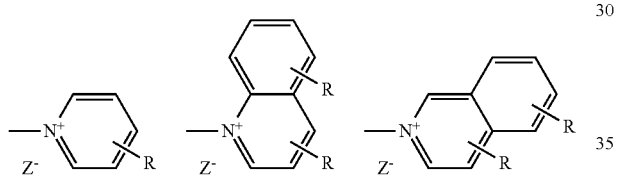

where each R stands for H or C$_{1-4}$-alkyl, Z stands for Cl, Br, I, CH$_3$SO$_3$, CF$_3$SO$_3$, CH$_3$PhSO$_3$, PhSO$_3$, R$^1$, R$^2$ and R$^3$ each stand, independently of one another, for H, C$_{1-30}$-alkyl, Ar or —CH$_2$Ar and Ar stands for an unsubstituted or mono- or polysubstituted aromatic ring or condensed ring systems having 6 to 18 C atoms in which, in addition, one or two CH groups are optionally replaced by N, a nonionic group selected from: linear or branched alkyl, where one or more non-adjacent C atoms may be replaced by O, S, and/or N; —OH; —SH; —O-(glycoside)o; —S-(glycoside)o; —OCH$_2$—CHOH—CH$_2$—OH; —OCH$_2$Ar(—NCO)p; —OAr(—NCO)p; —CR═CH$_2$; —OCOCR═CH$_2$; amine oxide; a group of one of the following formulae

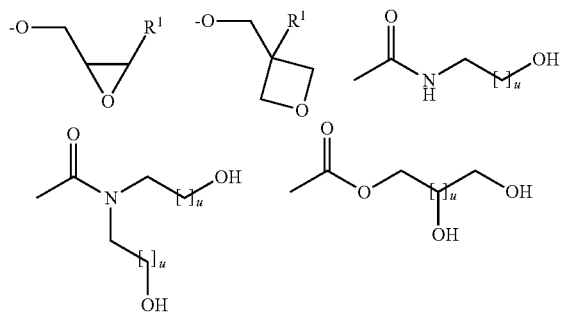

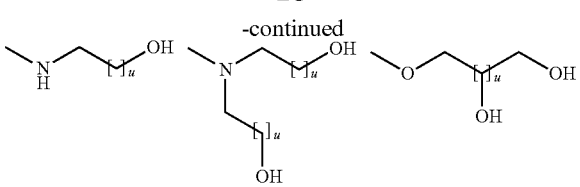

wherein, u stands for an integer from the range from 1 to 6, o stands for an integer from the range from 1 to 10, p stands for 1 or 2, R1, R2 and R3 each stand, independently of one another, for C$_{1-30}$-alkyl, Ar or —CH$_2$Ar, and Ar stands for an unsubstituted, mono- or polysubstituted aromatic ring or condensed ring systems having 6 to 18 C atoms in which, in addition, one or two CH groups are optionally replaced by C═O, and, glycoside stands for an etherified carbohydrate, and R stands for H or methyl; or an amphoteric group selected from the functional groups of the acetyl-diamines, the N-alkylamino adds and the betaines.

2. A formulation according to claim 1, wherein the compound of the formula (I) is a compound of the formulae (II), (III) and/or (IV):

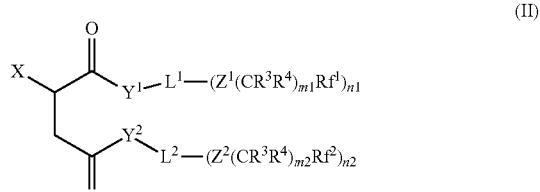

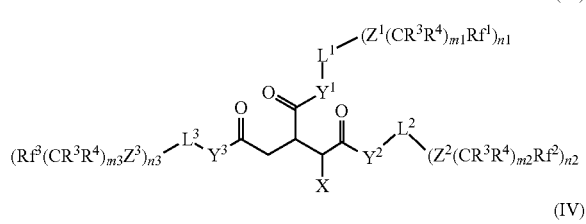

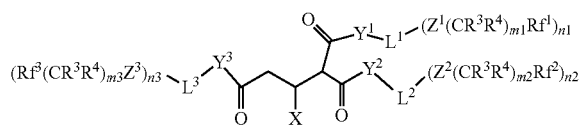

where

X is equal to —SO$_3^-$, —OSO$_3^-$, —PO$_3^{2-}$ or OPO$_3^{2-}$,

Y$^1$, Y$^2$, Y$^3$, Z$^1$, Z$^2$ and Z$^3$ are equal to O,

Rf$^1$, Rf$^2$ and Rf$^3$ are equal to perfluorinated alkyl groups having 1 to 4 C atoms, n1, n2 and n3 are equal to 1 or 2, m1, m2 and m3 are equal to 1-4, L$^1$, L$^2$ and L$^3$ are equal to linear or branched C3-C6-alkylene, and R$^3$ and R$^4$ are equal to hydrogen or an alkyl group having 1 to 3 C atoms.

3. A formulation according to claim 1, characterised in that the compounds of the formula (I) are compounds of the formulae (III-1) and/or (III-2):

(III-1)

[Structure of formula III-1: a compound with three R-O-C(=O) groups attached to a carbon chain with SO₃Na]

R = [structure: CH₃-CH(CH₃)-CH₂-O-CH₂-CF₂-CF₂-F with F substituents]

(III-2)

[Structure of formula III-2: similar to III-1 with three R-O-C(=O) groups and SO₃Na]

R = [structure: CH₃-CH(CH₃)-CH₂-O-CH₂-CF₂-CF₂-CF₂-F with F substituents]

where the * indicates the point of attachment of the R group.

4. A formulation according to claim 1, which further comprises at least one compound of the formula (VI)

$$(RF\text{-}(spacer)_m)_n M \quad (VI)$$

where
RF is a fluorine-containing group,
spacer is a single bond or an organic functional carbon chain,
n is ≥1,
m=0-1 and
M is an anionic, cationic, amphoteric or non-ionic group.

5. A formulation according to claim 4, characterised in that the group $(RF\text{-}(spacer)_m)_n\text{-}$ in the compounds of the formula (VI) is equal to $C_nF_{2n'+1}-$, $C_nF_{2n'+1}-CH_2CH_2-$, $C_nF_{2n'+1}-OCF_2CF_2-$, $C_nF_{2n'+1}-OC_6H_4-$, $C_nF_{2n'+1}-C(O)NH(CH_2)_3N=$, $C_nF_{2n'+1}-SO_2NH(CH_2)_3N=$, $CF_3CCl_2(CF_2CFCl)_{n'-1}-CF_2-$ or $C_8F_{17}CH_2CH_2Si(CH_3)_2-$, where n'=4-12, and M is equal to $-OPOO^-$, $-COO^-$, $-SO_3^-$, $-OSO_3^-$, $-OP(O)(O^-)O-$ or $-OP(O)O_2^{2-}$, and the compound of formula (VI) has $H^+$, $Na^+$, $K^+$, $Li^+$ or $NH_4^+$ as counterion.

6. A formulation according to claim 2, which comprises at least one compound of the formula (III) and at least one compound of the formula (VI)

$$(RF\text{-}(spacer)_m)_n M \quad (VI)$$

where
RF is a fluorine-containing group,
spacer is a single bond or an organic functional carbon chain,
n is ≥1,
m=0-1 and
M is an anionic, cationic, amphoteric or non-ionic group.

7. A formulation according to claim 1, which further comprises at least one compound of the formulae (VII) to (X)

(VII)

[Structure: Na⁺ ⁻O₃S-CH(-C(=O)-O-CH(C₂H₅)-C₄H₉)-CH₂-C(=O)-O-CH(C₂H₅)-C₄H₉]

(VIII)

[Silicone structure with Si-O-Si-O-Si-O-Si chain, with R group, and x, y repeating units]

where x=1-500, y=1-500 and R=phenyl, methyl or $-(O-C_2H_3R')_{n''}-OR''$, where n''=1-1000, R'=linear and branched alkyl radical and R''=linear and branched alkyl radicals, $$M_2D'(E_{n''}P) \quad (IX)$$

where $M=(CH_3)_3SiO-$, $D'=Si(R''')$, $E=-OCH_2CH_2$, n'''=5-40 and $P=-OH$, $-OMe$, or $-OAc$, where R'''=linear and/or branched alkyl chain, (X)

[Structure of an acetylene diol ethoxylate with two symmetric branches containing isobutyl groups and ethylene oxide chains terminated with H]

where n=1-100.

8. A formulation according to claim 4, which further comprises at least one compound of the formulae (VII) to (X)

(VII)

[Structure: Na⁺ ⁻O₃S-CH(-C(=O)-O-CH(C₂H₅)-C₄H₉)-CH₂-C(=O)-O-CH(C₂H₅)-C₄H₉]

(VIII)

[Silicone structure with Si-O-Si-O-Si-O-Si chain, with R group, and x, y repeating units]

where x=1-500, y=1-500 and R=phenyl, methyl or $-(O-C_2H_3R')_{n''}-OR''$, where n''=1-1000, R'=linear and branched alkyl radical and R''=linear and branched alkyl radicals, $$M_2D'(E_{n''}P) \quad (IX)$$

where M=(CH$_3$)$_3$SiO—, D'=Si(R'''), E=—OCH$_2$CH$_2$, n'''=5-40 and P=—OH, —OMe, or —OAc, where R'''=linear and/or branched alkyl chain,

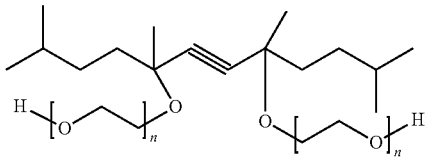
(X)

where n=1-100.

9. A formulation according to claim 1, characterised in that it is in the form of a liquid pesticide formulation which can be applied by means of spraying methods.

10. A formulation according to claim 1, which comprises one or more crop-protection agents.

11. A pesticide and/or crop-protection method which comprises applying a pesticide and/or crop protection agent formulation according to claim 1 to a crop or plant.

12. A method according to claim 11, which comprises applying the formulation by spraying in the cultivation of a crop or ornamental plant.

13. A method according to claim 11, wherein the compound of the formula (I) improves the efficacy of the pesticide and/or crop-protection agent and/or acts as dispersant, emulsion stabiliser and/or foam inhibitor.

14. A pesticide and/or crop-protection method which comprises applying a pesticide and/or crop-protection agent formulation according to claim 2 to a crop or plant.

15. A pesticide and/or crop-protection method which comprises applying a pesticide and/or crop protection agent formulation according to claim 3 to a crop or plant.

16. A formulation according to claim 1, wherein, in formula (I), X is: an anionic group X selected from —COO—, —SO$_3$, —OSO$_3$, —PO32-, —OPO$_{32}$, —(OCH$_2$CH$_2$)s-O—(CH$_2$)—COO—, —(OCH$_2$CH$_2$)s-O—(CH$_2$)t-SO$_3$, —(OCH$_2$CH$_2$)s-O—(CH$_2$)t-OSO$_3$, —(OCH$_2$CH$_2$)s-O—(CH$_2$)t-PO3$^{2-}$, —(OCH$_2$CH$_2$)s-O—(CH$_2$)t-OPO$_{32}$— or from the formulae A to C,

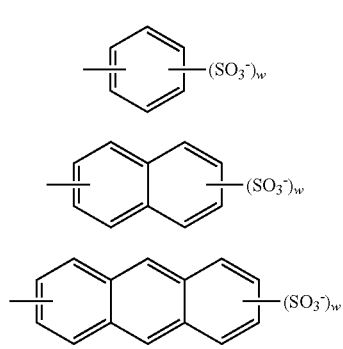

where s stands for an integer from the range from 1 to 1000, t stands for an integer selected from 2, 3 or 4 and w stands for an integer selected from 1, 2 or 3, having a monovalent cation selected from H+, an alkali metal cation or NR$_4$+, where each R is, independently, H or C1-C6-alkyl.

* * * * *